(12) United States Patent
Grass et al.

(10) Patent No.: US 11,177,030 B2
(45) Date of Patent: Nov. 16, 2021

(54) ESTIMATING FLOW, RESISTANCE OR PRESSURE FROM PRESSURE OR FLOW MEASUREMENTS AND ANGIOGRAPHY

(71) Applicant: Koninklijke Philips N.V., Eindhoven (NL)

(72) Inventors: Michael Grass, Hamburg (DE); Hanno Heyke Homann, Hannover (DE); Bram Antonius Philomena Van Rens, Utrecht (NL); Peter Maria Johannes Rongen, Eindhoven (NL); Melike Bozkaya, Amsterdam (NL); Roland Wilhelmus Maria Bullens, Mierlo (NL); Arjen Van Der Horst, Tilburg (NL)

(73) Assignee: KONINKLIKE PHILIPS N.V., Eindhoven (NL)

( * ) Notice: Subject to any disclaimer, the term of this patent is extended or adjusted under 35 U.S.C. 154(b) by 418 days.

(21) Appl. No.: 15/764,878

(22) PCT Filed: Sep. 27, 2016

(86) PCT No.: PCT/EP2016/072885
§ 371 (c)(1),
(2) Date: Mar. 29, 2018

(87) PCT Pub. No.: WO2017/055228
PCT Pub. Date: Apr. 6, 2017

(65) Prior Publication Data
US 2018/0286517 A1    Oct. 4, 2018

(30) Foreign Application Priority Data

Sep. 29, 2015 (EP) ..................................... 15187350

(51) Int. Cl.
*G16H 30/20* (2018.01)
*G16H 40/63* (2018.01)
(Continued)

(52) U.S. Cl.
CPC ............. *G16H 30/20* (2018.01); *G16H 30/40* (2018.01); *G16H 40/63* (2018.01); *G16H 50/50* (2018.01)

(58) Field of Classification Search
CPC ........................ G16H 50/50; G06Q 50/22–24
See application file for complete search history.

(56) References Cited

U.S. PATENT DOCUMENTS

| 7,970,187 B2 | 6/2011 | Puts et al. |
| 9,129,053 B2 | 9/2015 | Mansi et al. |

(Continued)

FOREIGN PATENT DOCUMENTS

| WO | 2012021307 A2 | 2/2012 |
| WO | 2013171644 A1 | 11/2013 |

(Continued)

OTHER PUBLICATIONS

Hu et al.: "Flow Resistance of Vessels with an Enlarged Cross-Sectional area in the Midsection"; The Open Circulation & Vascular Journal; Oct. 11, 2013. (Year: 2013).*

(Continued)

*Primary Examiner* — John A Pauls

(57) ABSTRACT

Systems and related methods to estimate, for a liquid dynamic system, flow or resistance based on a model of an object and pressure measurements collected in-situ at said object. Alternatively, pressure flow measurements are collected and pressure or resistance is being estimated.

12 Claims, 4 Drawing Sheets

(51) Int. Cl.
*G16H 30/40* (2018.01)
*G16H 50/50* (2018.01)

(56) References Cited

U.S. PATENT DOCUMENTS

| | | | |
|---|---|---|---|
| 2003/0120150 A1* | 6/2003 | Govari | A61B 5/0031 600/424 |
| 2011/0071404 A1 | 3/2011 | Schmitt | |
| 2013/0246034 A1* | 9/2013 | Sharma | A61B 6/503 703/11 |
| 2015/0201849 A1* | 7/2015 | Taylor | A61B 5/0044 600/508 |
| 2015/0257725 A1 | 9/2015 | Ohishi | |

FOREIGN PATENT DOCUMENTS

| | | |
|---|---|---|
| WO | 2014106186 A2 | 7/2014 |
| WO | 2014167511 A1 | 10/2014 |

OTHER PUBLICATIONS

Sabee Molloi, et al., "Estimation of coronary artery hyperemic blood flow based on arterial lumen volume using angiographic images", International Journal of Cardiovascular Imaging 28 (2012), pp. 1-11.

Kern, Morton J, et al., "Current concepts of integrated coronary physiology in the catheterization laboratory", Journal of the American College of Cardiology 55, 3 (2010), pp. 173-185.

Gould, K Lance, et al., "Anatomic versus physiologic assessment of coronary artery disease: role of coronary flow reserve, fractional flow reserve, and positron emission tomography imaging in revascularization decision-making", Journal of the American College of Cardiology 62, 18 (2013), pp. 1639-1653.

ComboWire Guide Wire by Volcano Inc., http://www.volcanocorp.com/products/combowire-xt.php.

* cited by examiner

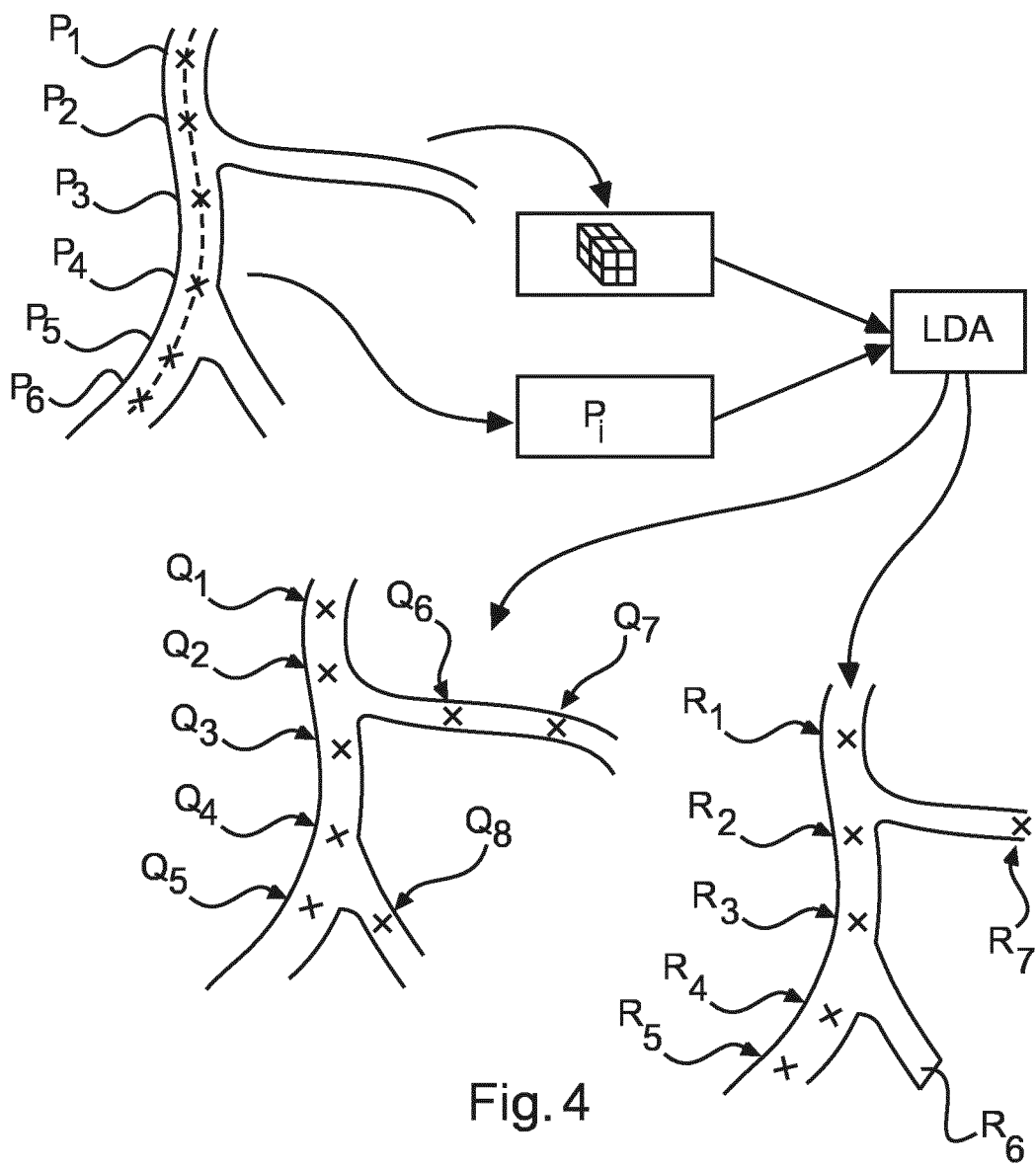
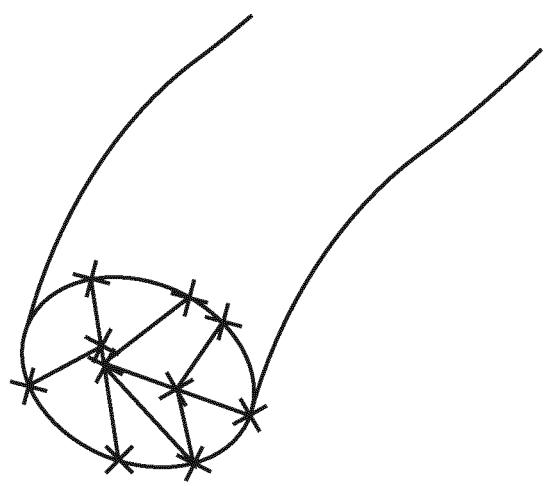
Fig. 4
Fig. 5

ESTIMATING FLOW, RESISTANCE OR PRESSURE FROM PRESSURE OR FLOW MEASUREMENTS AND ANGIOGRAPHY

CROSS-REFERENCE TO PRIOR APPLICATIONS

This application is the U.S. National Phase application under 35 U.S.C. § 371 of International Application No. PCT/EP2016/072885, filed on Sep. 27, 2016, which claims the benefit of European Patent Application No. 15187350.2, filed on Sep. 29, 2015. These applications are hereby incorporated by reference herein.

FIELD OF THE INVENTION

The invention relates to estimation systems for fluid dynamics, to estimation methods, to a computer readable media, and to computer program elements.

BACKGROUND OF THE INVENTION

Invasive catheter-based velocity measurement techniques have recently received increasing attention in functional stenosis assessment (e.g., in coronary arteries), especially in combination with pressure measurements by so-called "Combo-wires". These are guide wire systems that include measurement components such as intra-vascular ultrasound transducers for velocity measurements. There are also flow measurement techniques based on temperature transducer readings.

However, these approaches may be considered unreliable, as flow can be measured only locally but flow varies strongly over a cross-sectional area.

Other methods for flow quantification include the use of PET (positron emission tomography) such as reported K L Gould et al in "Anatomic versus physiologic assessment of coronary artery disease: role of coronary flow reserve, fractional flow reserve, and positron emission tomography imaging in revascularization decision-making", Journal of the American College of Cardiology 62, 18 (2013), pp. 1639-1653. Yet another approach is based on angiographic densitometry as described for instance by S Molloi et al in "Estimation of coronary artery hyperemic blood flow based on arterial lumen volume using angiographic images", International Journal of Cardiovascular Imaging 28 (2012), pp. 1-11. But these techniques tend to be complicated (because of the need for system calibration and approximating scaling laws in case of the method by S Molloi) or expensive, or are not readily available.

SUMMARY OF THE INVENTION

There may therefore be a need for an alternative system or method to estimate flow or pressure or resistance in fluid dynamic systems.

The object of the present invention is solved by the subject matter of the independent claims where further embodiments are incorporated in the dependent claims. It should be noted that the following described aspect of the invention equally applies to the estimation methods, to the computer program elements and to the computer readable media. According to a first aspect of the invention there is provided an estimation system for fluid dynamics, comprising:

an input port for receiving
i) at least one fluid pressure measurement collected in-situ from a vessel tree, each pressure measurement being associated with a location within the vessel tree, and
ii) medical image data of the vessel tree;
a model builder for generating a 3D geometrical model derived from the medical image data;
a registration unit for spatially registering the at least one fluid pressure measurement to the generated 3D geometrical model based on its associated location, and
a liquid dynamics analyzer configured to compute, based on the 3D geometrical model of the vessel tree, at least one flow and/or resistance value with respect to said vessel tree, using the spatially registered pressure measurements as boundary conditions.

The step of computing the flow or resistance includes in particular using the measured and spatially registered pressure readings as boundary conditions for solution in CFD algorithms.

We propose a novel approach to estimate blood flow and/or resistance based on intra-vascular pressure measurements with a geometric model derived from medical image data.

The proposed system and method can be used with benefit in and alongside fractional flow reserve (FFR) contexts. FFR provides a way to assess functional stenosis severity. FFR is a reliable measure for grading the functional limitations induced by a stenosis. Based on the aortic pressure $P_a$ and the pressure $P_d$ distal to the stenosis, FFR is defined as the ratio $FFR=P_d/P_a$. FFR is a widely used index to assess the functional impact of a stenosis in the coronary arteries. Typically, FFR is measured in an invasive fashion, by advancing a pressure wire past the stenosis and measuring the pressure drop across the stenosis.

In one embodiment, the proposed system and method allows harnessing the pressure readings which are collected during a conventional FFR measurement anyway. The pressure measurements are combined with an image based (e.g., angiographic X-ray or computer tomography) assessment of the coronary vessel geometry. A computational model is used based on this imagery to deliver a more complete picture of the geometry of the coronary and/or myocardial condition, which FFR alone could not give. In other words, instead of competing with FFR, the invention improves and adds up to FFR and provides in addition flow or resistance information. The use of dedicated and additional flow measurements is not necessary. For present purposes it is enough then to only measure pressure (and not flow) which can be done relatively cheaply because the pressure sensitive instrumentation is in general cheap or cheaper than flow sensitive instrumentation. Flow information is computed instead based on easily obtainable in-situ pressure measurements. "Relatively cheap" as used herein is in relation to flow or combo-wires which are in general more expensive to build than mere pressure measurement device (also referred to a "pressure wires").

According to one embodiment, the model includes at least one location that represents a stricture in said object and wherein the model builder is reconfigured to modify the model to remove or a least mitigate said structure and wherein the fluid dynamics analyzer is configured is recompute the at least one flow and/or resistance value based on the modified model. In other words, in this embodiment proposed system can be used with benefit for virtual checks of future therapy effects to better understand their medical benefits. The object (e.g. vessel) can be "virtually repaired" by geometrically removing a stricture structure (such a stenosis) from the model and then the computations are rerun based on the modified model that now represents the vessel with mitigated stenosis or without stenosis. The benefits of the stenosis therapy can then be better assessed "virtually", that is, beforehand. In one embodiment of this virtual repair procedure, in any given branch of the vessel model, the readings downstream the (former) stenosis location are either retained as boundary conditions in the computations, or ignored as boundary conditions in the computations or, as a middle ground between these two extremes, the respective downstream readings are at least mitigated (be weighing) or modified for any stenosis that that one wishes to repair.

According one embodiment, the computations of flow or resistance can be extrapolated into branches of the vessel where no pressure measurements have been collected to extend the remit of the proposed approach to other parts of the model, in particular then whole of the model.

In general more than one values (scalar or vectorial) are computed for a plurality of measurement locations. The values together define respective spatial distribution which of the respective fluid dynamical quantity (flow, pressure or resistance).

According to one embodiment, the system according to either one of the two aspects comprises a visualizer configured to render on a display device a visualization of the computed flow, pressure or resistance distribution.

According to one embodiment, said visualization comprises a spatially resolved flow map, representing the flow distribution in association with positions within said object.

According to one embodiment, the image data includes angiography data or computed tomography data. Alternatively or in addition, intra-vascular optical coherence tomography data, MR data, or ultrasound data, in particular intravascular ultrasound data, may be used. Preferably the at least one fluid pressure measurement is collected during a fractional flow reserve procedure.

According to one embodiment, the system comprises an imaging apparatus for supplying said image data.

According to one embodiment, the system comprises a measurement device for introduction into the object for collecting the at least one pressure measurement inside the object. More particularly, said pressure measurement device is a catheter having at least one pressure sensor.

In a preferred embodiment, the catheter is provided at its head or tip with a tracker including a location transducer. Thus, for each pressure measurement, a spatial location to be associated with the measurement may be established with high accuracy. In accordance with the invention, this location data is used in registering the pressure measurements to the geometrical vessel model.

According to second aspect there is provided an estimation method, comprising:

receiving at least one fluid pressure measurement collected in-situ from an object, each measurement being associated with a location within the vessel tree;

receiving medical image data;

generating a 3D geometrical model derived from the image data;

registering the at least one fluid pressure measurement to the generated 3D geometrical model based on its associated location, and computing, based on the 3D geometrical model of said vessel tree, at least one flow and/or resistance value with respect to said vessel tree, using the spatially registered pressure measurements as boundary conditions.

Applications of the proposed methods and systems are mainly envisaged in the medical field, in particular cardiology. However that is not to say that other applications are excluded herein. First, the systems and methods may be used to estimate flow, pressure or resistance in other organs than the heart coronaries and the respective input measurements may be collected in other than FFR contexts. For instance, leg arteries may be analyzed. In a further extension, flow or pressure of urine in uro logical investigations such as in (VCMG) Videocystometrography may be computed instead of blood flow. Second, it is also outside the medical field where the proposed systems and methods may be practiced with benefit, for instance in geology such as in speleological exploration of underwater cave systems or other.

BRIEF DESCRIPTION OF THE DRAWINGS

Exemplary embodiments of the invention will now be described with reference to the following drawings wherein:

FIG. 4 shows an illustration of flow and resistance method; and

FIG. 5 is an illustration of a part of a vessel model.

DETAILED DESCRIPTION OF EMBODIMENTS

Figure 1:
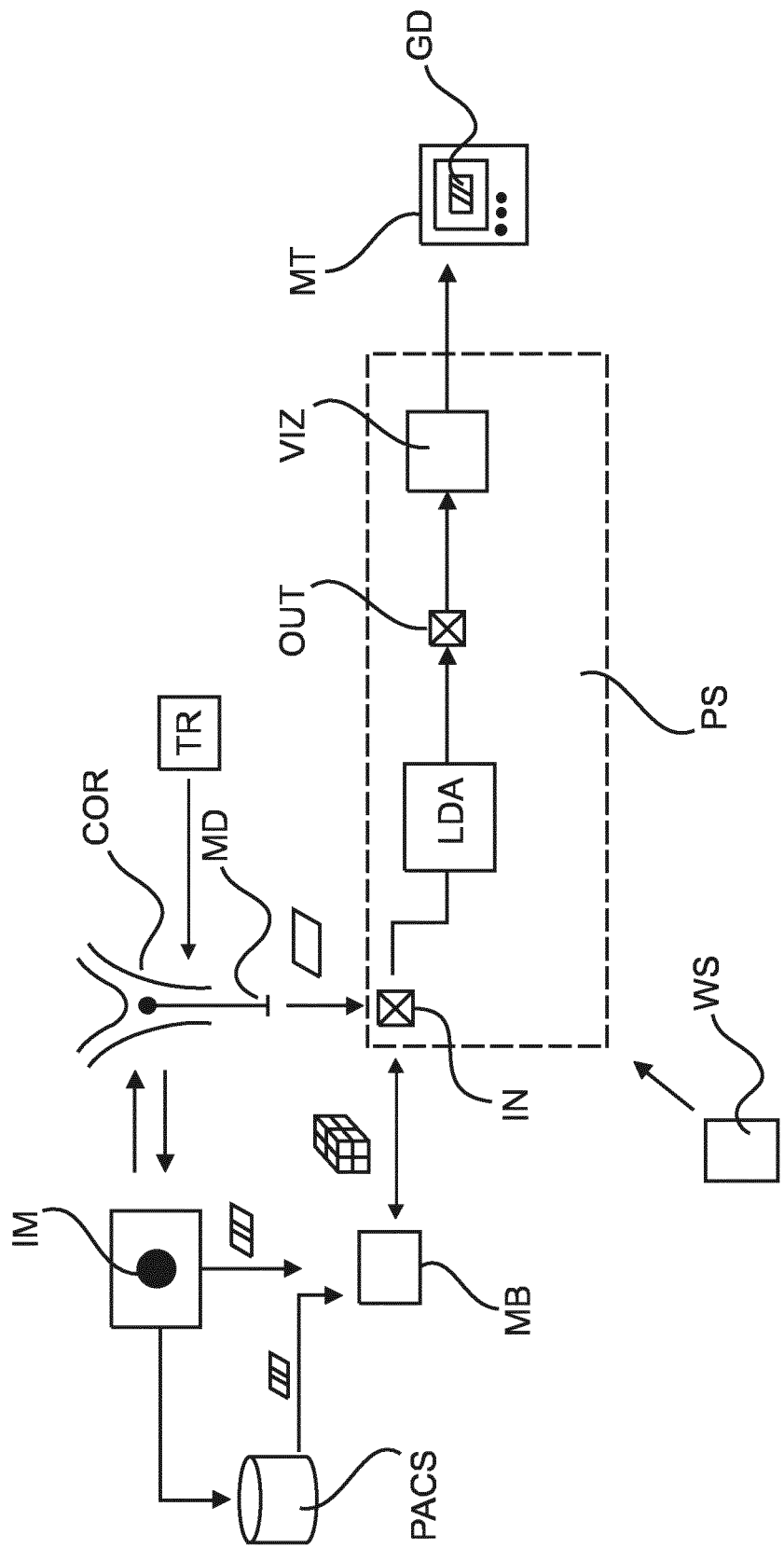
FIG. 1 shows a flow or pressure estimation system.

With reference to the schematic block diagram in FIG. 1 components of liquid dynamic analyzer system are shown.

The system can be used for volumetric flow or resistance estimation in an FFR context but applications other than in FFR, indeed even other than medical, are not excluded herein.

Briefly, and according to one embodiment the approach proposed herein can be used for blood flow measurement which combines intra-vascular pressure measurements with a geometric model of the vessel under investigation which is derived from medical image data. Advantageously, but not necessarily in all embodiments, the pressure measurements are those collected during a conventional FFR intervention with a suitable measurement device MD.

In more detail and with continued reference to FIG. 1, an imaging modality IM is used to acquire preferably, but not necessarily, 3D image data of an object of interest, for instance, of the coronary or periphery vessels COR of a human or animal patient. In one embodiment, the image data is generated in a rotational angiographic imaging run. Before, during or after the imaging, the measurement device MD such as a pressure wire is used to acquire in an interventional procedure, at a plurality of locations within or at the vessel system COR, respective pressure readings. The pressure wire is a steerable guide wire with a measurement head. The measurement head is formed from one or more pressure transducers/sensors mounted proximal to a tip portion of the guide wire MD. The pressure wire may also include a torque device to facilitate navigation through the vasculature. The wire MD may also include a tracking (sub-)system TR such as optical (shape sensing) electromagnetic tracking or the wire MD may be tracked in 3D using image processing of the supplied imagery and knowledge of the imaging geometry used by the imager IM.

Preferably, the readings include those collected across a stenosis in the vessel tree. For example, this may be done in a pull-back-sequence protocol during an FFR invasion. It will be understood that each pressure reading is in general associated or at least associable with a certain spatial location $X_i$ within the coronary COR at which the respective reading is acquired. This pressure-versus-location association is either generated automatically for instance using a location transponder of the tracker TR coupled to the head of the pressure wire. Alternatively, the locations can be computed from a given initial position of the measurement head and a given spatial sampling frequency (that is, how many measurements are taken per unit length) and a known measurement trajectory (which is indeed known for instance in a pullback measurement sequence).

The pressure readings and the image data are then forwarded as input to a processor section PC which can be implemented as a software module on a general purpose computer such as a workstation WS. Based on this input, the processor component of the proposed liquid dynamics analyzer system produces in one embodiment the desired volumetric blood flow and/or resistance data for the vessel system COR under examination.

The processing section PC receives the image data and the pressure readings at input port IN. From the image data, a 3D geometrical model (such as a mesh model, etc.) is generated by a model builder MB. This can be achieved in one embodiment by vessel segmentation, that is, segmentation based on image element (pixel, voxel) intensity. Alternatively, a 2D vessel angiogram can be segmented and based on the 2D curvature of the vessel, the projection geometry used by the imaging modality IM for the acquisition of the angiogram and the assumption of spherical vessel geometry a 3D vessel model is constructed. In other word, this allows building a 3D model from a single projection image. The model so generated and the pressure readings are then spatially registered onto each other by a registration unit (not shown). In other words, in the registration, respective locations associated with the pressure readings are made to correspond to respective geometrical points in the model. Registration can be either image based registration, manual registration or be may be based on the tracking data supplied by the tracker TR, if any.

The spatially registered readings are then forwarded to the liquid dynamics analyzer LDA component. This is arranged in one embodiment as a flow or resistance estimator which uses for instance computational flow dynamic (CFD) methods to compute volumetric flow values/estimates $Q_i$. The computed values are either scalar or a vector field.

More particularly, the acquired pressure readings are used as boundary conditions to compute the spatially resolved flow distribution. Whilst the model forms the geometrical constraints for the flow, pressured readings describe the flow locally. The relationship between volumetric flow and pressure is known to be governed by a system of partial differential equations such as Navier-Stokes equation or approximation thereof (e.g., a lumped parameter model). The type of equations is encoded into the flow estimator FE. The partial differential equations are spatially discretized by finite element methods into a potentially large set of ordinary differential equations which can then be then solved by various numerical techniques for the flow values. Solutions to the CFD problem can be generally described as vector fields $(p,\vec{Q})$ (p a position and $\vec{Q}$ being a velocity vector for the flow at that point). The vector fields are a collection of function and the boundary conditions prescribe through which points in phase space any possible solution must pass. That is, for any solution $(p,\vec{Q})$, the pressure at p must equal the pressure value P collected at said point p. The underlying CFD algorithm takes these constraints imposed by the boundary conditions into account.

If one is interested only in the magnitude (speed) of the velocity vectors as per the computed vector field solution, one can converted into a scalar field by taking absolute values of the vector component $(p, |\vec{Q}|=Q)$. Alternatively, using the lumped parameter model or other approaches one can compute the values directly as scalars.

In another embodiment, a lumped elements approach is described for instance in US 2011/0071404. The lumped elements approach has been shown to afford a quick turn-around. Any other CFD technique is also envisage herein. In one embodiment, the collection of the so computed volumetric flow values (in particular the speed at each point) together form a spatially resolved volumetric flow distribution for the model. That is, at each location of the model (which in turn corresponds to location within the object COR), the flow estimator unit associates a flow value (volume per second, such ml/s for instance).

The so estimated flow or resistance values are produced at an output port OUT as numerical values. Preferably the estimates are visualized by a visualizer VIZ and rendered for display on a monitor MT. More particularly, the flow estimates are displaced spatially resolved, that is, each estimate is shown associated with the respective location in the model or in the image data.

Figure 2:
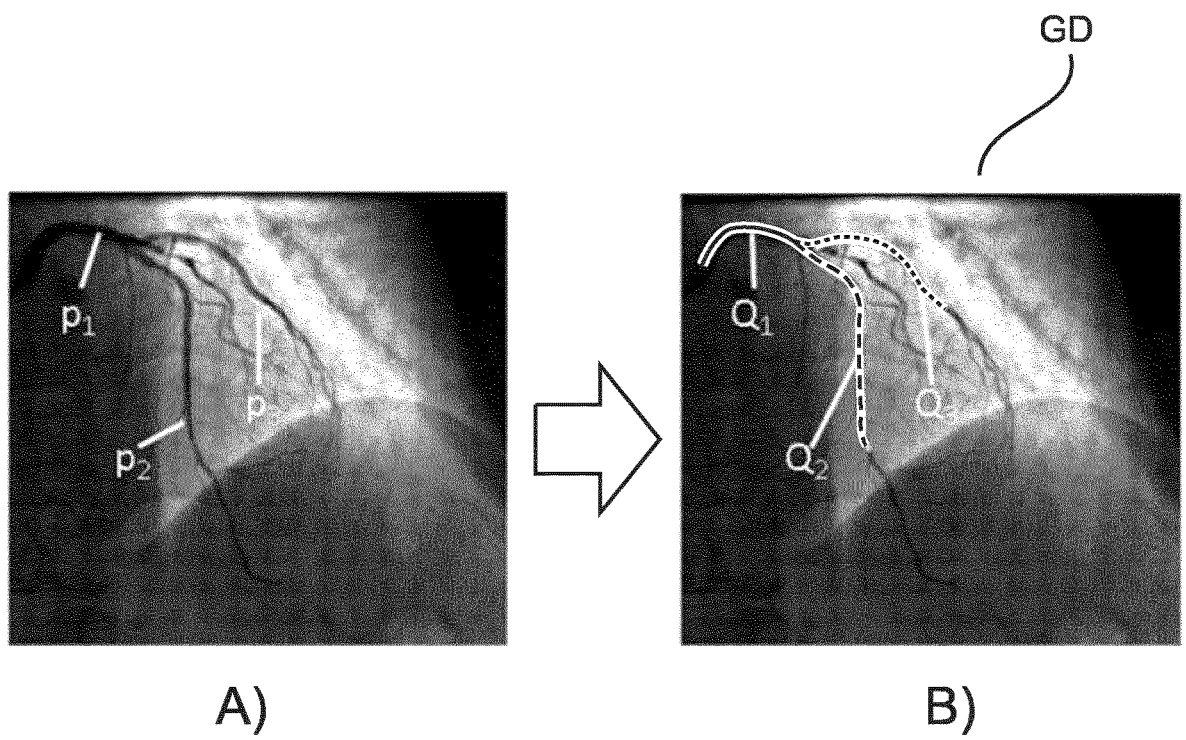
FIG. 2 shows a graphics display generated by the system in FIG. 1.

FIG. 2 shows in panel B) an example of a visualization GD of a spatially resolved flow estimate map based on pressure measurements p1, p2, p3 collected at different locations within the vessel COR which are shown diagrammatically in panel A). The visualization GD is formed from spatially arranged flow estimates Q1, Q2 and Q3 computed by the estimator FE. The flow estimate values $Q_i$ can be color-coded (shown in different line types: dotted, solid and dashed) and overlaid as shown in FIG. 2 B) on a reproduction of the image data or of the model. The graphics display in 2B) illustrates as an example a rather course discretization with only 3 measurement collections. Therefore, the model is broken up into three parts. More refined discretizations are also envisaged but in principle it would be sufficient to sample for merely 3 or even merely 2 pressure measurements.

It should be noted that the model builder MB may not necessarily operate to build the model from the image data itself. In an alternative approach a generic mesh model can be used which is then adapted according to the image data acquired from the object. For instance, iterative forward-projection-techniques can be used to deform the generic in a series iteration until the projections across the deformed generic model corresponds to the acquired image data (real projections). In this manner a generic model can be personalized or "tailored" to the image data of the object COR at hand.

To obtain more persuasive results in FFR it is advisable to acquire pressure readings in two states of the subject, one set in a state of stress and one set in a relaxed state. In other words, at some or each of the locations a pair of pressure readings are acquired: one in a stressed state and the other in a relaxed state of the subject.

In one embodiment wherein the model builder MB is reconfigured to modify the model to remove or a least mitigate a structural feature of the model and to then said structure (e.g. stricture such as in stenosis) and wherein the liquid dynamics analyzer LDA is configured is re-compute the flow value and/or resistance value based on the modified model. This operation will be explained in more detail below at steps S40a,b.

Figure 3:
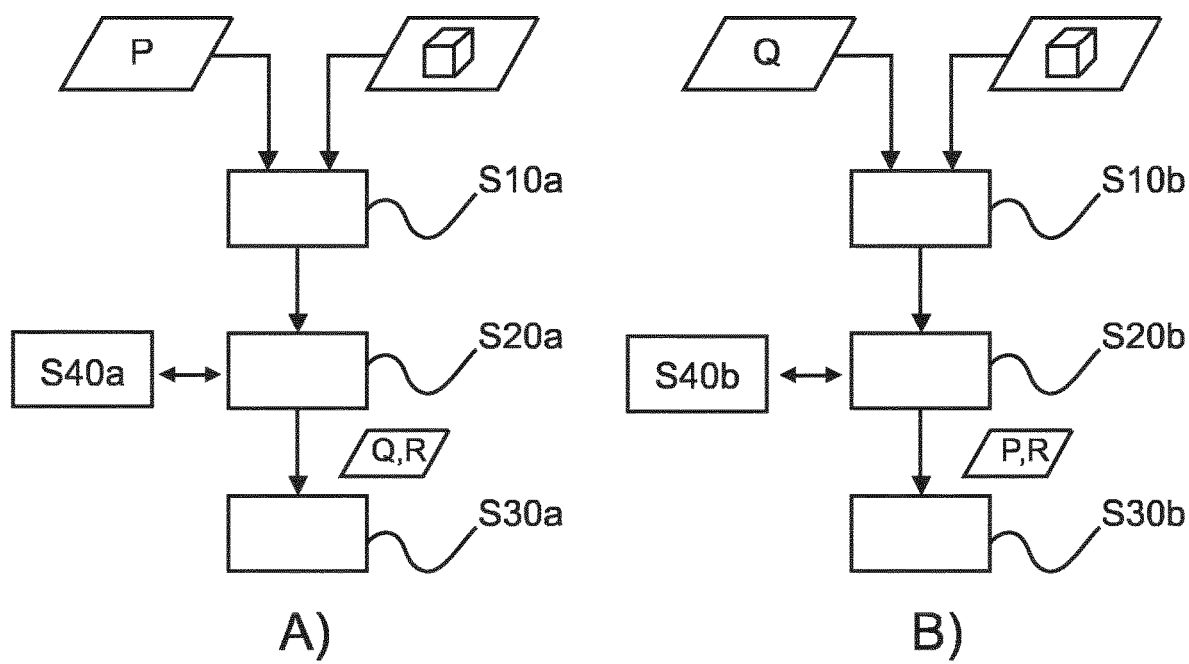
FIG. 3 shows a flow chart of a flow and pressure estimation methods.

With reference to FIG. 3 A), there is shown a flow chart of a liquid dynamics analyzing method, in particular a flow or resistance estimation method.

At step S10a a plurality of pressure measurements are collected in situ from or in an object at a plurality of locations. Multiple intra-vascular pressure measurements are taken using a catheter or guide-wire equipped with a pressure sensor. It has been shown to be beneficial that that at least some of the measurement points or locations (at which the pressure readings are collected in step S10a) include locations of at least one inlet and an at least one outlet of the geometric vessel model of the vessel tree. This allows making the computations in the follows up (step S20a) more realistic, even for other vessel segments in the tree. In addition thereto, in one embodiment, a respective pair of measurements are placed up and downstream any at least one or better still at any stenoses location.

At an optional step S20a, flow distribution for a liquid residing in or passing through the object is computed based on a model of said object and based on using the collected measurements as boundary conditions in a CFD solving algorithm.

It is also envisaged in some embodiments to extrapolate flow or resistance values into parts of the model that correspond to location (in a branch of vessel mode for instance) in the object where no measurements have been collected. This is done by using one or more of the boundary conditions also for parts of the model in respect of which no measurements have been collected. This can be done by using some of the boundary conditions at locations in said other parts that correspond structurally or functionally to the locations in the measured branch. For instance a boundary condition that is based on a measurement at an outlet point may be used at an outlet point in a different branch.

At (optional) step S30a the estimated values or the flow distribution is visualized on a display device.

Although in the above embodiment in-situ pressure measurements have been collected to compute volumetric flow values, a dual method to this is also envisaged and shown in flow chart B) with corresponding steps S10b-S30b. So, rather than collecting pressure measurement values in situ, it is flow measurement values that are collected in situ at step S10b, and a pressure distribution is then computed completely analogous to step S20a in step S20b. The pressure values can then be displayed as spatially resolved pressure distribution values at step S30b.

In either one of the above methods, A) and B), at least the positions of the measurements with respect to the 3D geometric model should be known. The model can be constructed from image data acquired from the object. 1. The image data is preferably 3D or stereoscopic. In case of X-ray angiography, a rotational sequence or two projections from different angles might be used. Possibly a single projection might also suffice when one uses assumption on cross-sectional shapes of the vessels. For instance, one may assume a priori circular vessel cross-sections. In some embodiments, a construction of a mere 2D model rather than a 3D model may also be sufficient. Another embodiment that can be based on uni-directional image data are densitometric methods where one predicts diameter in projection direction. See for instance US 2007/0053558A1 on densitometry. In principle different imaging methods than X-ray angiography can be used for generating the geometric vessel model. This applies especially to intra-vascular optical coherence tomography (OCT) or ultrasound (US) but might also include MRT and CT.

In the flow estimation embodiment, the volumetric flow (measured in volume/sec) values are computed as opposed to "point" speed values (measured in distance/length), the latter being usually produced by conventional flow measurement devices such as a combo-wire which measures both, flow and pressure. Point speed values which can be converted into volumetric data by multiplication with the respective vessel cross-section as per the geometry of the model at the location at which the flow measurement was collected.

Whereas flow velocity asks with which velocity (direction and speed) an imaginary point travels when suspended in the liquid under examination, volumetric flow asks for the amount of liquid that passed through an imaginary planar region positioned at any given location in the liquid. Volumetric flow data has been found to be more relevant for assessing tissue viability than flow in terms of velocity and more relevant than pressure.

The proposed method is especially sensitive in the presence of stenoses (when pressure drop from inlet to outlet occurs). However, it has been found less sensitive if the pressure drop is close to zero. Pressure measurement can be performed under normal conditions or during drug-induced hyperemia to increase the pressure loss along the vessel.

The proposed method and system may furnish a more reliable approach to volumetric flow measurement and can potentially replace expensive flow measurement with "Combo Wire" devices or PET measurements. "Combo-wires" include those measurement devices that allow measurement of both, pressure and flow.

A further refinement of the above proposed embodiments is to segment the image data into perfused sub-volumes for each branch of the vessel tree and to assign a calculated blood flow to each sub-volume. This can provide a "virtual perfusion map".

When coronary pressure measurements are taken under normal conditions and at hyperemia (i.e., in a relaxed state), the coronary flow reserve (CFR) index can be predicted from the calculated flow values. See for instance Kern, Morton J et al in "Current concepts of integrated coronary physiology in the catheterization laboratory", Journal of the American College of Cardiology 55, 3 (2010), pp. 173-185.)

In a yet further refinement, the pressure or flow measurements can be synchronized with an ECG signal, to so compute cardiac-phase-dependent flow or pressure, respectively. This may include utilizing a 4D (that is, 3D+time) coronary model. FIG. 4 is an illustration of the method as per A), FIG. 3. Pressure readings P1-P7 are collected at different locations. Based on a 3D model and using the measured pressure data as boundary conditions in a CFD algorithm, corresponding flow values Q1-Q5 are computed and, in addition, using the geometry of the model, flow Q6-Q8 can be extrapolated also into branches where no pressure measurement was collected. Alternatively and in a similar manner corresponding resistance values R1-R5 can be computed for a measured branch and interpolated values R6, R7 for other branches (where no measurements have been collected). For instance, as can be seen in FIG. 4 one extrapolates into other branches of the vessel model by using the reading P6 at the outlet of the measured branch as respective outlet reading boundary conditions for the other (non-measured) branches to so compute values Q6-Q8 and R7-R8, respectively.

The same procedure as described above in relation to FIG. 4 can be carried out analogously for method B) in FIG. 3 where flow measurements are collected and it is the pressure and/or resistance values that are computed (for an illustration of this embodiment, each "P" is exchanged for a "Q" in FIG. 4).

Yet another refinement combinable with any of the above described is illustrated in FIG. 5. The boundary conditions (that is, the pressure or flow measurements collected in situ) can be localized down to cross-sectional level as shown in the Figure, given the tracking information supplied by the tracker sub-system TR is detailed enough. So rather than merely assigning the boundary collection to a certain section in the vessel (which may be fine in some embodiments), the boundary condition is assigned along a certain radius in the that section to precisely "peg" the boundary condition at an appropriate distance from the vessel's wall in the respective vessel section. The boundary conditions can then be mapped to spatial nodes as per the CFD algorithms used. This refinement is particular advantageous in the embodiment of FIG. 3 B) where flow measurements are collected because these are known to vary along the cross-sectional radius, that is, with distance from the vessel wall. These locations are shown in FIG. 5 as 'X's in the shown exemplary cross section. For instance some 3D CFD algorithms use a 3D node system made up from a plurality of elements such as a tetrahedron or others that cover the space within a vessel. The spatial assignment, within the model's cross-section, of the measurements as boundary conditions to vertices or center points etc. of these node elements can be achieved by using the tracking information. The computations of the associated pressures can be expected to be more accurate. Also, these localization of boundary conditions can be expected to return more accurate results for the FIG. 3A) embodiment as well.

It would also be possible to "repair" the stenotic vessel with QCA (Quantitative Coronary Analysis), i.e. estimating the "healthy" vessel contour and redo the calculations, so that relative volume flows or pressures can be simulated. In one embodiment, in either one of the above methods A),B) in FIG. 3, the method includes a further step for the case where the model includes at least one location that represents a stricture such as a stenosis in the vessel object. This further step includes modifying S40a,b the model to remove or a least mitigate said structure and re-computing i) the at least one flow and/or resistance value or ii) the at least one pressure/and or resistance value, respectively, based on the modified model. In more detail, and referring to method A) in FIG. 3 for sake of definiteness, the method can be used with benefit for virtual checks of future therapy measure to better understand their medical benefits. The object (e.g. vessel) can be "virtually repaired" by geometrically removing or mitigating a stenosis from the model and then the computations of the CFD algorithm are rerun based on the modified model that represents the vessel with mitigated stenosis or without stenosis. The benefits of the stenosis therapy can then be better assessed "virtually", that is, beforehand. In other words, and according to one embodiment, the model builder MB may be (re)used to adapt the model by geometrically removing the respective strictures representing the respective stenoses. In one embodiment this is done by using the vessel cross-sections/width up and downstream the stricture to linearly (or higher-dimensionally) interpolate between the two to thereby geometrically eliminate the stricture. In this manner, a new, modified model is created that represents new geometrical boundary conditions.

The previously computed measurements are either retained as boundary conditions for the modified model or the reading(s) downstream/the now modified stenosis are ignored or are likewise adapted to mitigate the effect of these downstream boundary conditions. For instance, the boundary conditions may be multiplied by suitable weighting factors to implement this mitigation in the computations of the flow or resistances for the modified model. This virtual repair procedure can be also used analogously with the embodiments B) in FIG. 3 where pressure and/or resistances are being computed. Preferably, these adaptations of the respective boundary conditions are done downstream the (former or modified) strictures for any given branch of the vessel model where the stricture is located.

The methods or systems proposed above themselves to the functional assessment of all types of stenosis in the arteries of the human body including coronaries, iliac, femoral, brachial, and hepatic arteries as well as the carotids.

The components of the flow or pressure estimation system as per FIG. 1 may be arranged as separate modules in a distributed architecture and connected in a suitable communication network.

The components may be arranged as dedicated FPGAs or as hardwired standalone chips.

The components, and in particular the liquid dynamics analyzer LDA may be programmed in a suitable programming language such as C++ or C routines. Alternatively, higher level scientific computing platforms such as Matlab® or Simulink® may be used.

In another exemplary embodiment of the present invention, a computer program or a computer program element is provided that is characterized by being adapted to execute the method steps of the method according to one of the preceding embodiments, on an appropriate system.

The computer program element might therefore be stored on a computer unit, which might also be part of an embodiment of the present invention. This computing unit may be adapted to perform or induce a performing of the steps of the method described above. Moreover, it may be adapted to operate the components of the above-described apparatus. The computing unit can be adapted to operate automatically and/or to execute the orders of a user. A computer program may be loaded into a working memory of a data processor. The data processor may thus be equipped to carry out the method of the invention.

This exemplary embodiment of the invention covers both, a computer program that right from the beginning uses the invention and a computer program that by means of an up-date turns an existing program into a program that uses the invention.

Further on, the computer program element might be able to provide all necessary steps to fulfill the procedure of an exemplary embodiment of the method as described above.

According to a further exemplary embodiment of the present invention, a computer readable medium, such as a CD-ROM, is presented wherein the computer readable medium has a computer program element stored on it which computer program element is described by the preceding section.

A computer program may be stored and/or distributed on a suitable medium (in particular, but not necessarily, a non-transitory medium), such as an optical storage medium or a solid-state medium supplied together with or as part of other hardware, but may also be distributed in other forms, such as via the internet or other wired or wireless telecommunication systems.

However, the computer program may also be presented over a network like the World Wide Web and can be downloaded into the working memory of a data processor from such a network. According to a further exemplary embodiment of the present invention, a medium for making a computer program element available for downloading is provided, which computer program element is arranged to perform a method according to one of the previously described embodiments of the invention.

It has to be noted that embodiments of the invention are described with reference to different subject matters. In particular, some embodiments are described with reference to method type claims whereas other embodiments are described with reference to the device type claims. However, a person skilled in the art will gather from the above and the following description that, unless otherwise notified, in addition to any combination of features belonging to one type of subject matter also any combination between features relating to different subject matters is considered to be disclosed with this application. However, all features can be combined providing synergetic effects that are more than the simple summation of the features.

While the invention has been illustrated and described in detail in the drawings and foregoing description, such illustration and description are to be considered illustrative or exemplary and not restrictive. The invention is not limited to the disclosed embodiments. Other variations to the disclosed embodiments can be understood and effected by those skilled in the art in practicing a claimed invention, from a study of the drawings, the disclosure, and the dependent claims.

In the claims, the word "comprising" does not exclude other elements or steps, and the indefinite article "a" or "an" does not exclude a plurality. A single processor or other unit may fulfill the functions of several items re-cited in the claims. The mere fact that certain measures are re-cited in mutually different dependent claims does not indicate that a combination of these measures cannot be used to advantage. Any reference signs in the claims should not be construed as limiting the scope.

The invention claimed is:

1. An estimation system for fluid dynamics, comprising:
   an intravascular catheter or guidewire comprising a pressure sensor, wherein the intravascular catheter or guidewire is configured to, using the pressure sensor, collect a plurality of fluid pressure measurements in-situ from within a vessel tree;
   an input port for receiving:
      medical image data of the vessel tree, wherein the vessel tree includes a first branch and a different, second branch; and
      the plurality of fluid pressure measurements, wherein the plurality of fluid pressure measurements is collected in-situ from only the first branch, each of the plurality of fluid pressure measurements being associated with a location within the first branch where the pressure sensor collected the fluid pressure measurement;
   a model builder for generating a 3D geometrical model derived from the medical image data;
   a registration unit for spatially registering the plurality of fluid pressure measurements to the generated 3D geometrical model based on the associated locations within the first branch;
   a liquid dynamics analyzer configured to:
      automatically set first boundary conditions for the first branch based on the spatially registered plurality of fluid pressure measurements and the associated locations within the first branch;
      compute, based on the 3D geometrical model and the first boundary conditions, at least one of a first flow value or a first resistance value with respect to the first branch; and
      extrapolate at least one of a second flow value or a second resistance value to the second branch; and
   an output port configured to output, to a display in communication with the output port:
      the medical imaging data;
      a visualization of the plurality of fluid pressure measurements overlaid on the first branch in the medical imaging data;
      a visualization of at least one of the first flow value or the first resistance value overlaid on the first branch in the medical imaging data; and
      a visualization of at least one of the second flow value or the second resistance value overlaid on the second branch in the medical imaging data, wherein, to extrapolate, the liquid dynamics analyzer is configured to:
         automatically set second boundary conditions for the second branch based on the first boundary conditions and the 3D geometrical model; and
         compute, based on the 3D geometrical model and the second boundary conditions, at least one of the second flow value or the second resistance value with respect to the second branch.

2. Estimation system of claim 1, wherein the geometrical model includes at least one location that represents a stricture in the first branch, and wherein the model builder is configured to:
   apply a weighting factor to one or more of the first boundary conditions based on the stricture to modify the 3D geometrical model and simulate a therapy,
   wherein the liquid dynamics analyzer is configured to recompute at least one of the first flow value or the first resistance value based on the modified 3D geometrical model for evaluating a benefit of the therapy.

3. Estimation system of claim 1, wherein the medical image data includes angiographic X-ray data or computed tomography data.

4. Estimation system of claim 1, further comprising an imaging apparatus for supplying said medical image data.

5. Estimation system of claim 1, wherein a head of the intravascular catheter or the guidewire is provided with a tracker including a location transponder, for establishing the location to be associated with a fluid pressure measurement of the plurality of fluid pressure measurements.

6. The estimation system of claim 1, wherein the associated locations correspond to a respective position along the vessel tree and a respective radius within a cross-section of the vessel tree at the position.

7. The estimation system of claim 1, wherein the first flow value comprises a cardiac-phase dependent flow value.

8. An estimation method, comprising:
   receiving a plurality of fluid pressure measurements collected in-situ from only a first branch of a vessel tree by an intravascular a pressure sensor of an intravascular catheter or guidewire positioned within the vessel tree positioned within only the first branch, each of the plurality of fluid pressure measurements being associated with a location within the first branch where the pressure sensor collected the fluid pressure measurement;
   receiving medical image data of the vessel tree including the first branch and a different, second branch;

generating a 3D geometrical model derived from the medical image data;
registering the plurality of fluid pressure measurements to the generated 3D geometrical model based on the associated locations within the first branch;
automatically setting first boundary conditions for the first branch based on the registered plurality of pressure measurements and the associated locations within the first branch; and
computing, based on the 3D geometrical model and the first boundary conditions, at least one of a first flow value or a first resistance value with respect to the first branch;
extrapolating at least one of a second flow value or a second resistance value to the second branch, wherein the extrapolating comprises:
automatically setting second boundary conditions for the second branch based on the first boundary conditions and the 3D geometrical model; and
computing, based on the 3D geometrical model and the second boundary conditions, at least one of the second flow value or the second resistance value with respect to the second branch; and outputting, to a display:
the medical imaging data;
a visualization of the plurality of fluid pressure measurements overlaid on the first branch in the medical imaging data;
a visualization of at least one of the first flow value or the first resistance value overlaid on the first branch in the medical imaging data; and
a visualization of at least one of the second flow value or the second resistance value overlaid on the second branch in the medical imaging data.

9. Method as per claim 8, wherein the 3D geometrical model includes at least one location that represents a stricture in the first branch, and wherein the method includes:
applying a weighting factor to one or more of the first boundary conditions based on the stricture to modify the 3D geometrical model and simulate a therapy; and
re-computing at least one of the first flow value or the first resistance value based on the modified 3D geometrical model for evaluating a benefit of the therapy.

10. Method as per claim 8, wherein pressure measurements of the plurality of fluid pressure measurements are collected across a stenosis in the first branch of the vessel tree.

11. Method as per claim 10, wherein the pressure measurements are collected at least at a location of at least one inlet and a location of at least one outlet of the first branch.

12. A computer program product comprising:
a non-transitory computer-readable medium having computer program elements recorded thereon for:
receiving a plurality of fluid pressure measurements collected in-situ from only a first branch of a vessel tree by a pressure sensor of an intravascular catheter or guidewire positioned within the vessel tree, each of the plurality of fluid pressure measurements being associated with a location within the first branch where the pressure sensor collected the fluid pressure measurement;
receiving medical image data of the vessel tree including the first branch and a different, second branch;
generating a 3D geometrical model derived from the medical image data;
spatially registering the plurality of fluid pressure measurements to the generated 3D geometrical model based on the associated locations within the first branch;
automatically setting first boundary conditions for the first branch based on the spatially registered plurality of fluid pressure measurements and the associated locations within the first branch; and
computing, based on the 3D geometrical model and the first boundary conditions, at least one of a first flow value or a first resistance value with respect to the first branch; extrapolating at least one of a second flow value or a second resistance value to the second branch, wherein the extrapolating comprises:
automatically setting second boundary conditions for the second branch based on the first boundary conditions and the 3D geometrical model; and
computing, based on the 3D geometrical model and the second boundary conditions, at least one of the second flow value or the second resistance value with respect to the second branch; and outputting, to a display:
the medical imaging data;
a visualization of the plurality of fluid pressure measurements overlaid on the first branch in the medical imaging data;
a visualization of at least one of the first flow value or the first resistance value overlaid on the first branch in the medical imaging data; and
a visualization of at least one of the second flow value or the second resistance value overlaid on the second branch in the medical imaging data.

* * * * *